United States Patent [19]

Shashoua

[11] Patent Number: 4,933,324

[45] Date of Patent: Jun. 12, 1990

[54] FATTY ACID-NEUROACTIVE DRUG CONJUGATE AS A PRODRUG

[76] Inventor: Victor E. Shashoua, 176 Tappan St., Brookline, Mass. 02146

[21] Appl. No.: 315,134

[22] Filed: Feb. 24, 1989

Related U.S. Application Data

[63] Continuation-in-part of Ser. No. 160,667, Feb. 26, 1988.

[51] Int. Cl.$^5$ .................. A61K 37/02; A61K 31/44; C07C 103/52; C07D 221/18
[52] U.S. Cl. ........................ 514/17; 514/284; 514/400; 514/415; 514/549; 514/627; 530/302; 530/323; 546/75; 548/342; 548/504; 548/507; 560/144; 564/204; 564/207
[58] Field of Search ............ 548/342, 504, 507; 560/144; 564/204, 207; 514/400, 415, 549, 627, 17, 284; 546/75; 530/330, 323, 302

[56] References Cited

PUBLICATIONS

*Chemical Abstracts*, 76:97365c (1972), [G. Dhopeshwarkar et al., *Biochim. Biophys. Acta*, 1972, 255(2), 572–9].
*Chemical Abstracts*, 108:92100g (1988), [R. Spector, *J. Neurochem.*, 1988, 50(2), 639–43].
*Chemical Abstracts*, 106:90177x (1987) [Jpn. Kokai Tokkyo Koho, JP 61,204,136, 9/10/86].
T. Higuchi et al., (Editors), *Prodrugs as Novel Drug Delivery Systems*, Acs Symposium SEries, vol. 14, Acs, Washington, 1975, pp. 14–15.

*Primary Examiner*—Richard A. Schwartz
*Attorney, Agent, or Firm*—Wolf, Greenfield & Sacks

[57] ABSTRACT

The invention involves the formation of a prodrug from a fatty acid carrier and a neuroactive drug. The prodrug is stable in the environment of both the stomach and the bloodstream and may be delivered by ingestion. The prodrug passes readily through the blood brain barrier. Once in the central nervous system, the prodrug is hydrolyzed into the fatty acid carrier and the drug to release the drug.

In a preferred embodiment, the carrier is 4, 7, 10, 13, 16, 19 docosahexa-enoic acid and the drug is dopamine. Both are normal components of the central nervous system. The covalent bond between the drug and the carrier preferably is an amide bond, which bond may survive the conditions in the stomach. Thus, the prodrug may be digested and will not be hydrolyzed completely into the carrier molecule and drug molecule in the stomach.

48 Claims, 2 Drawing Sheets

FATTY ACID-NEUROACTIVE DRUG CONJUGATE AS A PRODRUG

BACKGROUND OF THE INVENTION

This application is a continuation in part of Patent Application Serial No. 07/160,667 dated Feb. 26, 1988 and entitled DOPAMINE ANALOG AMINE.

This invention relates in general to the fields of medicine, pharmacology and biochemistry, and more particularly to prodrugs capable of delivering a drug across the blood brain barrier including a prodrug made of a fatty acid-dopamine conjugate that is effective as an appetite-suppressant.

There are many obstacles to developing treatments which allow the delivery of a drug to an active site in the body. Ingestion of a drug often is not possible because many drugs will not survive the environment of the stomach. Thus, easy and safe self-administration of many drugs is not available. A drug, of course, may be injected directly into the blood stream of a patient. However, because some drugs do not survive for very long in the bloodstream, frequent injections at great inconvenience to a patient may be necessary. The inability of a drug to survive in the bloodstream may be overcome in certain instances by increasing the dosage or by increasing the frequency of administration. However, increasing the dosage can result in undesirable side effects and increasing the frequency of administration only adds inconvenience.

The delivery of a neuroactive drug to the central nervous system (CNS) via the bloodstream involves an extraordinary obstacle; the drug must be capable of crossing the blood brain barrier. The blood brain barrier may loosely be regarded as a biological exclusion barrier involving both passive and active transport, which barrier controls the exchange of materials between the plasma and the central nervous system. Many drug substances are unable to pass through this barrier in efficacious amounts or at all. Thus, there is a serious need for a mechanism for introducing a drug across the blood brain barrier and into the CNS.

Efforts have been taken to enhance the ability of certain drugs to pass through the blood brain barrier. Investigators have attempted to mask the polar groups of a drug to produce more lipophilic derivatives, as lipophilic compounds are believed to cross the blood brain barrier more readily than hydrophilic compounds. For example, diacetyl and triacetyl esters of dopamine and norepinephrine have been made to mask the hydroxyl groups of these compounds and produce more lipophilic derivatives. This investigator has formed an ester bond between δ-aminobutyric acid, a drug which is unable to cross the blood brain barrier, and a "carrier" molecule having an enhanced ability to cross the blood brain barrier. The carrier-drug conjugate shares with the carrier the ability to cross the blood brain barrier. Once in the CNS, the conjugate itself may be active. However, it is believed that the ester bond between the carrier and drug is broken in the CNS to release the drug in its native form. This may occur due to the general presence of active, non-specific esterases throughout the CNS.

Appetite-suppressant drugs have been sought for many years. Dopamine is believed to be involved in the neuropathways responsible for appetite-suppression. Dopamine itself is not used as an appetite-suppressant because it does not readily cross the blood brain barrier. Drugs which closely resemble the structure of dopamine and which will cross the blood brain barrier have been used with some success as alternatives to dopamine.

The most widely used appetite-suppressant drugs are generally based on derivatives of amphetamine, which structurally resembles dopamine and has some properties which correspond to a dopamine agonist. Unlike dopamine, sufficient uptake of amphetamines across the blood brain barrier does occur to produce a biological effect. However, amphetamines have many serious cardiovascular and neuropsychiatric side effects, as well as a tendency to develop tolerance, the increasing resistance to the usual effect of the drug over time. At worst, tolerance to a drug renders the drug useless. At best, tolerance generally encourages the use of higher drug doses, increasing the possibility of undesirable side effects. In animal tests, tolerance to certain of these amphetamine derivatives has been shown to develop within one day after one dose. Using amphetamine itself, tolerance has been shown to develop within 3-15 days.

Dopamine is also known to play a crucial role in several neurologically related disorders. For example, Parkinsonism is a striatal dopamine deficiency. Because dopamine (and related catacholamines) does not cross the blood brain barrier Parkinsonism is treated with L-Dopa, a precursor to Dopamine. This treatment, however, is at the expense of a wide variety of undesireable side effects, including hallucination. Dopamine agonists which are used in the treatment of hyperprolactinemia associated with pituitary adenomas or amenorrhea also induce undesireable side effects. Thus, there is a serious need for delivering dopamine itself or dopaminergic agents directly to the brain.

SUMMARY OF THE INVENTION

The invention involves the formation of a prodrug from a fatty acid carrier and a neuroactive drug. The prodrug is stable in the environment of both the stomach and the bloodstream and may be delivered by ingestion. The prodrug passes readily through the blood brain barrier. The prodrug has a brain penetration index of at least two times the brain penetration index of the drug alone. Once in the central nervous system, the prodrug, which preferably is inactive, is hydrolyzed into the fatty acid carrier and the drug. The carrier preferably is a normal component of the central nervous system and is inactive and harmless. The drug, once released from the fatty acid carrier, is active.

Preferably, the fatty acid carrier is a naturally occurring, partially-saturated straight chain molecule having between about 16 and 26 carbon atoms, and more preferably 20 and 24 carbon atoms. Most preferably, the carrier is the all cis form of 4, 7, 10, 13, 16, 19 docosahexa-enoic acid.

The covalent bond between the drug and the carrier preferably is an amide bond, which bond may survive the conditions in the stomach. Thus, the prodrug may be ingested and will not be hydrolyzed completely into the carrier molecule and drug molecule in the stomach.

Most preferably, the drug is dopamine, also a normal component of the central nervous system and the prodrug is Compound 8739 may be expressed alternatively as This compound has been found to be useful as an appetite-suppressant. It has a brain penetration index of 33, crossing the blood brain barrier eight times as well as dopamine. It is inactive until it crosses the blood brain barrier and hydrolyzes to release dopamine into the central nervous system. The drug suppresses appetite without harmful side effects and without inducing tolerance. The prodrug also appears to be capable of delivering the dopamine preferentially into the synaptosomal membranes, the location of the drug action.

It is an object of the invention to provide an appetite-suppressant drug that will not induce tolerance and will not cause harmful side effects.

Another object of the invention is to provide a carrier molecule capable of being combined with a drug to form a prodrug that will readily cross the blood brain barrier and allow release of the drug into the central nervous system.

Another object of the invention is to provide a prodrug that is stable in the environment of the stomach and in the bloodstream.

Another object of the invention is to provide an amide derivative of dopamine with biological activity useful in the regulation of appetite.

Another object of the invention is to provide pharmalogical compositions comprising amides of the carrier of the invention combined with neuroactive drugs, and particularly dopamine.

Still another object of the invention is to provide a method for delivering a neuroactive drug, including dopamine, to the central nervous system.

Yet another object of the invention is to provide a method for regulating appetite.

Yet a further object of the invention is to provide a method for treating neurological disorders in general, and specifically for introducing dopamine and dopaminergic agents into the brain to treat dopamine related disorders such as Parkinsonism and hyperprolactinemia.

DETAILED DESCRIPTION OF THE PREFERRED EMBODIMENTS AND OF THE DRAWINGS

The most preferred embodiment of the invention is

This compound has extraordinary and unexpected properties. This compound, hereinafter called compound 8739, is inactive until it crosses the blood brain barrier to release dopamine into the central nervous system (CNS). Unlike dopamine, compound 8739 survives sufficiently in the environment of the stomach and the bloodstream and therefore can be administered orally.

Compound 8739 has an enhanced ability to cross the blood brain barrier, with a brain penetration index (BPI) of about 33, as compared to about 4 for dopamine. It is inactive as a prodrug in that it does not bind to either D-1 or D-2 dopamine receptors. Rather, once in the central nervous system, dopamine is released as an active fragment of compound 8739. In addition, compound 8739 is taken up into the synaptosomal membranes preferentially, the synaptosomal membranes being the site of activity for the dopamine. This property may contribute to the compound's desirable properties.

Once dopamine is released as an active fragment, it produces effects on food intake and on general locomotor activity in mice in a dose-dependent manner. Food intake decreased by as much as 50% at the higher doses. Open field activity also decreased by about 50%, indicating that, unlike amphetamine, compound 8739 has a tranquilizing effect rather than an activity-enhancing effect.

Many of the undesirable side effects of amphetamines were absent. Compound 8739 failed to induce "stereotypy", failed to produce an effect on "circling behavior" of striatal lesioned rats, and failed to demonstrate any diverse effects on motor function or motivation in test animals. Remarkably, there was no indication of tolerance. Failure to induce tolerance was unexpected.

Another favorable property of compound 8739 was unexpected. Previous reports have demonstrated that fatty acids, including the fatty acid of compound 8739, induce swelling of the brain. Chan, P. H., Fishman, R. A., SCIENCE, Vol. 20, 358–360 (1978). Compound 8739 (and another prodrug compound made from a straight chain fatty acid having 20 carbon atoms and 4 double bonds), however, did not induce any swelling.

EXPERIMENTAL DATA

Synthesis of the Compound 8739

Compound 8730 is synthesized as follows:

DHA is first converted to DHA anhydride in the presence of dicyclohexyl carbodiimide. This is then reacted with dopamine in the presence of 4-dimethylaminopyridine as the acid acceptor in tetrahydrofuran. In a typical experiment 300 mg of DHA (0.009 M) was dissolved in a mixture of 3 ml hexane and 4 ml benzene and stirred under nitrogen. Next, a solution of 0.00615 M of dicyclohexyl carbodiimide in 4 ml benzene (0.1267 g) was stirred together with the DHA for 3 hr at room temperature. A white precipitate of dicyclohexyl urea formed as the reaction proceeded. The dicyclohexyl urea was filtered off to give a clear solution of the anhydride in benzene. This was concentrated down to 2 ml in a rotary evaporator and diluted with 10 ml of tetrahydrofuran (dry). The freshly prepared anhydride was then added to a solution of dopamine hydrobromide (0.1053 g) (or 0.005 M) in the presence of 0.009 M of 4-diethylaminopyridine (0.098 g). The initially cloudy mixture after stirring for 30 min at room temperature gave a mixture of a clear liquid and a brown precipitate. At the end of the reaction, 0.2 ml of water was added to the mixture, and stirring was continued for an additional 30 min to completely hydrolyze any remaining unreacted anhydride. The liquid phase was isolated and evaporated to dryness to yield a brown viscous solid. This was then dissolved in 70% ethanol in water (25 ml), and the solution was then passed through a mixed-bed ion exchange resin containing a strong acidic resin based on polystyrene sulfonic acid and a strong basic resin based on quanternary amonium substituents such as tetramethyl amonimum hydroxide (RG501, Fisher Scientific, Cambridge, Mass.) using 90% ethanol in water as the eluent. This resin removes from the mixture unreacted dopamine, dimethylaminopyridine, as well as the liberated DHA molecule. The effluent from the column (a pale yellow solution) was then evaporated in a rotary evaporator to give a solid. The product was recrystallized from aqueous ethanol (yield =75%).

The structure of compound 8739 (III) was established by mass spectrometry. The major peak (95% of the compound) consisted of a product with a mass of 550. Fragment analysis by mass spectrometry and carbon, hydrogen, infrared, and NMR spectra confirmed the structure of compound 8739.

A trimethyl silyl derivative (compound IV) of the two hydroxyl groups of dopamine was also synthesized to further confirm the structure of compound 8739. This derivative was shown to have the correct mass of 608.

Compound 8739 was stored as a solution in ethanol (12 mg/ml) in the cold. Aliquots of this were evaported to dryness and dissolved in 15% propylene glycol in 0.1 M $NaHCO_3$ for use in biological activity tests.

Brain Uptake Studies

A brain penetration index (BPI) determination was used as a criterion for measuring the capacity of a compound to cross the blood brain barrier. Shashoua, V. E., Jacob, J. N., Ridge, R., Campbell, A. and Baldessarini, R. J., *J. Med. Chem.* 27, 659 (1984). The BPI is a measure of the uptake of a compound by the brain relative to its uptake by the liver. The liver is chosen as a reference since it is an organ which has no barrier to diffusable molecules present in the blood. Moreover, even if subcutaneous injections are used, the injected material tends to remain largely at the site of the injection and slowly diffuse into the circulation. Therefore, the amount of material in the liver will reflect the amount available rather than the initial dose injected.

Measurements of the quantity of the drug present in the brain and liver were measured at five minutes after a subcutaneous injection and were used to calculate the BPI, the equation being:

$$BPI = [brain[/[liver] \times 100$$

For these measurements, compound 8739 was synthesized from $^{14}C$-labeled dopamine. Thirty $\mu Ci$ of labeled dopamine hydrochloride was mixed with 0.1 mg of unlabeled dopamine hydrobromide and reacted with a two fold excess of DHA anhydride. The reaction was run overnight; the product was then evaporated to dryness and dissolved in ethanol. The compound was identified as 8739 by its migration properties on thin-layer chromatography using chloroform:methanol as one solvent and dimethylformamide (DMF) as the other. The migration properties were equivalent to those of the unlabeled product.

$^{14}C$-labeled 8739 was dissolved in 15% propylene glycol in 0.1 M $NaHCO_3$ and then injected subcutaneously (s.c.) into male balb C mice (20 ±2 g). After 5 minutes the animals were sacrificed by cervical fracture and the brain and liver were dissected out, weighed and homogenized in 8 and 10 ml of Brain Protein Solvent (BPS) buffer, respectively [BPS =2% sodium dodecyl sulfate in 0.03 M Tris, 6 M urea, pH 7.6, 0.01 M EDTA and 0.14 N NaCl]. Aliquots were then counted for $^{14}C$ content in 10 ml of a liquid scintillation fluid, Liquiscent (National Diagnostic Company, Somerville, N.J.) using a Beckman liquid scintillation counter. The $^{14}C$ counts were then used to calculate the total quantity of compound 8739 present in the brain per gram of tissue as compared to that in the liver. The ratio of the amount in the brain as a percent of that present in liver was determined.

RESULTS
TABLE I

| Compound | Brain (cpm/g) | Liver (cpm/g) | BPI Value (%) |
|---|---|---|---|
| 8739 | 1305 | 4300 | 30 |
| 8739 | 1297 | 3931 | 33 |
| Dopamine | | | 4 |
| D-glucose | | | 33 |

The results indicate that the brain uptake of compound 8739 is over eight-fold higher than the brain uptake for dopamine. Compound 8739 also compares favorably with glucose which is reported in the literature to have a BPI index of 33.

Studies of the Pattern of Distribution of 8739 in Membranes of the Central Nervous System The utility of a drug may be determined by its ability to be taken up selectively by the particular regions of the brain upon which the drug acts. A study was made to determine the pattern of distribution of compound 8739 in the various membranes in the central nervous system. Approximately $2 \times 10^6$ counts of $^{14}$C-labeled 8739 in 0.3 ml of 15% propylene glycol in 0.1 M NaHCO$_3$ was injected subcutaneously into test mice (20±2 g). After 30 minutes the animals were sacrificed by cervical fracture; the brain was then removed and homogenized in 4 ml of isotonic medium (0.14 N NaCl, 0.03 M Tris pH 7.4 containing 1.5 mM calcium acetate) according to the method of Whittaker (Whitaker V. P. Biochem J., 72 694–706 [1959]). The fraction P1 containing nuclear and cell membrane components was sedimented for 5 min at 2,500 rpm at 0° C. The supernatant containing the crude synaptosomal fraction was next centrifuged at 13,000 rpm for 30 min to yield a pellet containing the crude synaptosomal fraction (P2). P1 and P2 were then dissolved in BPS, and the amount of label and protein in each fraction was determined.

Results
TABLE II

| | CPM/mg Protein after 30 min of Uptake | | |
|---|---|---|---|
| Expt. No. | P$_1$ (Nuclear and Cell Membrane Fraction) | P$_2$ (Crude Synaptosomal Fraction) | P$_2$/P$_1$ |
| 1 | 2.7 | 5.2 | 1.9 |
| 2 | 2.7 | 5.6 | 2.1 |
| 3 | 4.19 | 12.5 | 2.9 |

As shown in Table II, the uptake of compound 8739 into the crude synaptosomal fraction (P2) was greater by a factor of an average of 2.3 than in the P1 fraction (nuclear and cell membrane fraction). This suggests that there is a preferential concentration of the compound into the synaptic fraction P2, indicating that 8739 is more highly associated with nerve endings, as would be expected from the natural distribution of DHA in lipid glycerides in such membranes.

PHARMACOLOGICAL PROPERTIES

Open-field motor activity measurement

The effect of compound 8739 on general motor activity was determined. The general motor activity of balb-c mice was measured in a Stoelting electronic activity monitor apparatus during a 90-min period following an intraperitoneal injection of the compound as a solution in 15% propylene glycol in 0.1 M NaHCO$_3$. A detailed description of the apparatus is reported in Stewart R. J., Campbell A., Spark G. and Balessarini R. J. Psychopharmacol. 60, 281 (1979).

The test group (six mice) received an i.p. injection of the drug in a vehicle (15% propylene glycol in 0.1 M NaHCO$_3$, a total volume of between about 1–0.3 ml). The six control mice received the same volume of vehicle, but no drug. The results (Shown in FIG. 1,) are expressed as the percent decrease in open field activity for the test group versus the control group. The results indicate that compound 8739 depresses the activity of the mice by as much as 50%, demonstrating that compound 8739 is biologically active following its uptake into the brain. The response was dose dependant with higher doses of compound 8739 resulting in a greater decrease in general motor activity.

FOOD CONSUMPTION MEASUREMENTS

Figure 1:
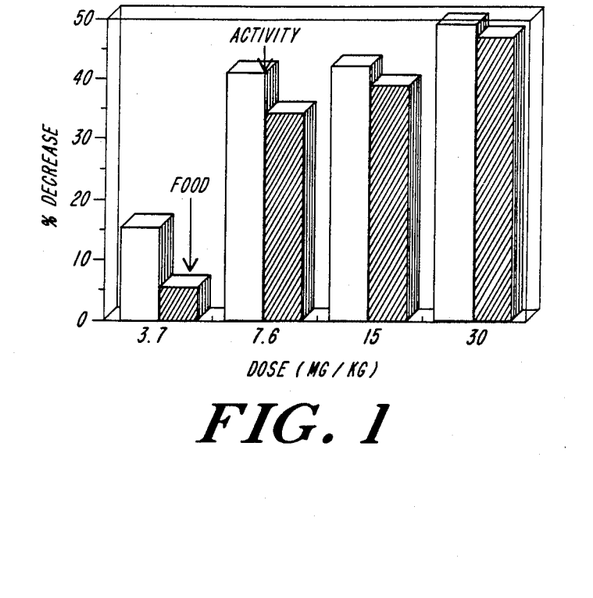
FIG. 1 is a graph showing the effect of the produrg of the preferred embodiment on motor activity and food intake of mice.

The effect of compound 8739 on food consumption was determined for balb-c mice that were food deprived for 24 hr, with water freely available. The six test mice were given an i.p. injection of compound 8739 as a solution in 15% propylene glycol in 0.1 M NaHCO$_3$, a total volume of between about 0.1–0.3 ml. The six control mice received the same volume of vehicle, but no drug. The quantity of "mouse chow" eaten during the 60-min period following the injections was determined. The results, also shown in FIG. 1, are expressed as the percent decrease in food consumption for the test group versus the control group. The results indicate that compound 8739 is an appetite suppressant (40–50% decrease in food intake). The decrease was dose dependent, with higher doses of compound 8739 causing greater decrease in food intake. The same experiment was conducted using oral administration of compound 8739. The results were the same.

Figure 2:
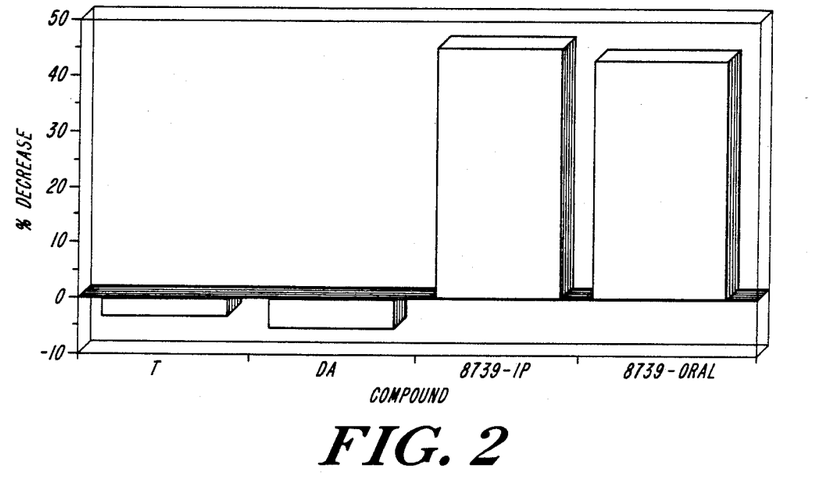
FIG. 2 is a graph comparing the effect on motor activity in mice of varying the mode of delivery of the prodrug of the preferred embodiment.

Determination of the Effect of Mode of Delivery of Compound 8739 on Open Field Activity The effects of the mode of delivery of Compound 8739 (oral vs. i.p.) on the general open-field activity of mice (n=6) was assessed. As shown in FIG. 2, the drug was as active when ingested as when injected. A 40–50% decrease in activity occurred when either delivery method was employed. No significant changes in open-field activity occurred when either the carrier molecule (T) or dopamine (DA) is administered at the same dose.

Evaluation of Circling Behavior

Dopamine agonists such as apomorphine and amphetamine cause circling behavior in animals with nigrostriatal lesions. Compound 8739 releases dopamine following proteolysis by central nervous system enzymes. It was expected that compound 8739 would cause circling behavior in animals with nigrostriatal lesions in a manner similar to that of dopamine agonists.

Unilateral nigrostriatal lesions in rats were produced by administering unilateral injections of 6-OH dopamine into the nigrostriatum pathway. Seven days later, these animals were i.p. injected with the test drugs and circling behavior was recorded as rotations per minute during a 30-min period in the test apparatus, Ungerstedt U. and Arbathnott G. W., *Brain Res.* 24, 485–493 (1970).

TABLE III

| COMPOUND | DOSE (mg/kg) | AVERAGE ROTATION SCORES (Rotations/minutes) | |
|---|---|---|---|
| | | Ipsilateral | Contralateral |
| Apomorphine | 0.1 | 0.1 | 4.8 |
| Apomorphine | 0.5 | 0 | 13.7 |
| Amphetamine | 3.0 | 2.5 | 0.4 |
| Amphetamine | 5.0 | 3.32 | 0.92 |
| 8739 | 34 | 0.08 | 0.05 |
| 8739 | 51 | 0.08 | 0.12 |
| Controls (uninjected) | | 0.10 | 0.12 |

Apomorphine produced a rapid circling behavior to the contralateral side of the lesion, whereas amphetamine caused circling rapidly to the ipsilateral lesion side. The enhanced contralateral rotations for apomorphine and ipsilateral rotations for amphetamine are consistent with the reported results for these dopamine agonists. Compound 8739 did not evoke this behavior. Rather, the rate of circling was very low, approximately the same as that observed for uninjected controls. Thus it appears that compound 8739 does not evoke all of the effects (side effects) of dopamine agonists.

SELF-STIMULATION DATA

A self-stimulation test has been used to measure the capacity of a given pharmacological agent to inhibit rats from receiving self-induced electrical stimuli via electrodes implanted in their brains (lateral hypothalamus). Stellar J. R. and Stellar E., *The Neurobiology of Motivation and Reward*, Springer-Verlag, N.Y., 1985. Animals will press levers to receive a pulse of current from the implanted electrode at a rate dependent upon the quantity of current that is being delivered as a reward. It is believed that the reward obtained results from the release of dopamine caused by the electrical stimulation (Stellar J. R.). The intensity of the current is varied by raising the frequency at which 250 mV pulses (0.1 msec duration) are delivered during a 0.5-sec time span. A plot of the log of the frequency of the delivered pulses vs. the rate of level press for an animal gives the self-stimulation reward curve. Injections of drugs which have a neuroleptic-type or tranquilizing effect can depress the rate of self-stimulation, shifting the response to higher current deliveries. Pemozide can give a depressed rate by about 90%. Investigations of the efficacy of compound 8739 by this test showed that the compound had no effect on either the reward or the motor aspect of the self-stimulation parameters. This indicates that compound 8739, even though it is able to cause a decrease in the general motor activity of an animal, has no effect on the motivation or the capacity to press for the "current reward". The animal continues to press the lever at the rate equivalent to a non-injected control or one receiving the vehicle alone. Thus, compound 8739 does not produce yet another effect (side effect) characteristic of dopamine agonists.

TESTS FOR TOLERANCE

The effects of daily i.p. injections of compound 8739 at a dose of 20 mg/kg on open field activity and food consumption was tested to determine whether tolerance to the drug was induced over time. The open field activity of six test mice and six control mice was monitored for five days. Then, the test mice were given i.p. injections of the drug in a vehicle and the control mice were given i.p. injections of the vehicle only. This regimen was carried out for a 21 day test period. At the end of the 21 days, the vehicle alone was given daily to both test and control mice and open field activity and food consumption was monitored for an additional six days.

Figure 3:
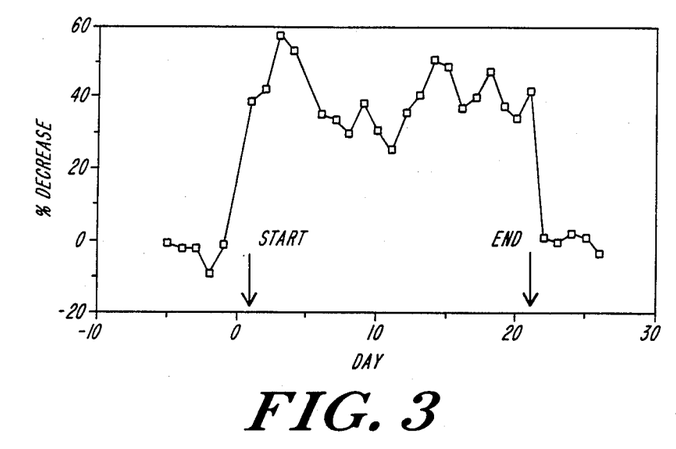
FIG. 3 is a graph showing the effect on motor acitivity in mice of long term administration of the prodrug of the preferred embodiment.

FIG. 3 plots the percent decrease in open field activity of the test mice (n=6) as compared to the controls (n=6). As shown in FIG. 3, the level of activity prior to injections was the same for both groups. Upon initation of injections, there was a 30% to 60% decrease in open field activity. This decrease remained fairly constant for the entire 21 days of injections indicating that no tolerance was induced by repeated injections during the test period. Beginning at day 22 and daily until day 27, vehicle alone was given to both groups. As shown in FIG. 3, activity returned to its predrug level when the drug administration was discontinued.

The effect of long-term administration of compound 8739 on the pattern of food consumption of mice was compared to the long-term effects of the administration of amphetamine. Daily i.p. injections of compound 8739 (20 mg/kg) were given to rest animals and daily i.p. injections of amphetamine (2 mg/kg) were given to control animals for 21 days. 24 hours after the first injection and about every five days after that, the animals were food-deprived for 24 hours with water freely available, and then were tested for food consumption for one-hour beginning at five minutes after receiving their daily injection.

Figure 4:
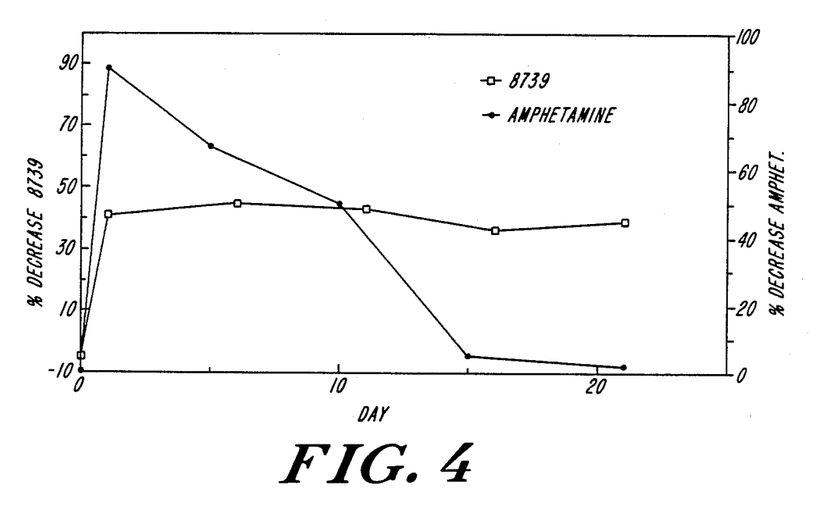
FIG. 4 is a graph comparing the effect on food intake in mice of long term administration of the prodrug of the perferred embodiment with amphetamine.

FIG. 4 plots the percent decrease in food consumption versus time. For amphetamine injected mice, the decrease in food intake due to the amphetamine virtually disappeared after 15 days indicating complete tolerance to the dosage employed. With compound 8739 injected mice, the approximately 40%–50% decrease in food intake persisted for the entire 21 day period indicating no tolerance had developed.

The pharmacological properties of compound 8739 appear to be in part characteristics of a dopamine agonist. Compound 8739 depresses the general motor activity and food intake behavior in mice. However, many of the properties which might be considered as "side effects" of dopamine agonists such as amphetamine and apomorphine are not obtained. Thus, circling behavior in nigrostriatal lesion to animals and motivational effects in self-stimulation experiments do not result following the administration of compound 8739.

Compound 8739 may be administered orally without any apparent loss in efficacy, and, therefore, is stable. Moreover, the compound does not bind to the dopamine receptors in receptor binding assays. Thus, the drug appears to be inactive until proteolysis releases the active dopamine. While the mechanism of action of the drug is not fully understood, and the inventor does not intend to be bound by any theory, it is believed that the localization of uptake into synaptic endings may cause site-specific release of the active dopamine from the prodrug. Such site-specific release could be responsible for some of the favorable properties of the drug. Further, that the carrier and drug are natural constituents of the CNS may contribute to compound 8739's desirable properties.

The invention is not limited to the foregoing description of the preferred embodiment. Thus, it is contemplated that the specific carrier described in the preferred embodiment and other carriers of the invention described in greater detail below are capable of being linked by an amide bond or otherwise to other neurotransmitters, analogues of neurotransmitters including analogues of dopamine and other neuroactive substances to facilitate the delivery of the substance across the blood brain barrier and into the CNS.

The preferred carrier also has been coupled to a Met-enkephalin derivative of the following formula YGGFMK, in which the carrier is coupled via a peptide bond to the gamma amino group of lysine (K). This compound, when injected into mice at a dose of 20 mg/kg body weight, was effective as an analgesic at a tenfold lower dose as compared to the carrier free Met-enkephalin (Paw Lift Latency Hotplate Test). The preferred carrier has also been coupled via an amide bond to the free amino group of norepinephrin. This compound had an eightfold higher BPI than norepinephrin. The list of other useful neuroactive substances is well-known to those skilled in the art and includes, but by no means is limited to: neurotransmitters such as dopamine, serotonin, δ-aminobutyric acid, norepinephrine, histamine and epinephrine; neuroactive amino acids acids such as glycine, aspartic acid, glutamic acid and taurine; and anorectic compounds such as amphetamine, phefluoramine, and diethylpropion. Although the CNS uptake of the anorectic compounds is satisfactory, when these compounds are coupled to the preferred carriers localized delivery of these compounds into the synaptosomal membranes of the CNS is facilitated.

In addition to the above listed substances, it will be recognized by one of ordinary skill in the art that drug compounds such as anti-AIDS substances, anti-cancer substances, antibiotics and other drugs capable of acting within the central nervous system may be coupled to the carriers of this invention and delivered to the brain.

The drug compound and carrier may be coupled using a variety of reactions involving treating the neuroactive compound (or a protected derivative thereof) having one, free hydroxyl or amino group with the corresponding fatty acid carrier or an activated derivative thereof. For example, a dopamine derivative having its two hydroxyl groups protected with acetonide may be reacted with the carrier in the presence of a water-removing compound such as dicyclohexyl carbodiimide in a solvent such as dioxane, tetrahydrofurane and methylpyrrolidone or N,N dimethylformamide at ambient temperature. The solvent then may be removed and the desired product may be extracted from the formed dicyclohexylurea using a suitable solvent such as methylene chloride. The protecting group then may be removed by treatment with a suitable acid such as 4N HCl in dioxane. The amine group of a neuroactive compound may be coupled to the carboxyl group of the carrier also by using the acid chloride or a low carbon ester derivative of the carrier and forming amide bonds by liberating HCl or an alcohol respectively. Drugs containing alcohol groups (OH) may be coupled via ester bonds to the fatty acid carrier by similar procedures as described above (e.g. using the anhydride derivative, the acid chloride derivative for the free acid of the carrier). Alternate couplings such as phosphoramide, sulfate, sulfonate, phosphate or urethane also may be used as will be recognized by one of ordinary skill in the art to coupled carrier molecules to drugs.

Amide bonds are preferred for coupling because they may survive the environment of the stomach and the prodrug may be administered orally. However, it should be recognized that bonds incapable of surviving the environment of the stomach such as an ester bond still may be used to link the carrier of the invention and a drug, with the resulting conjugate capable of crossing the blood brain barrier. Such a prodrug may be injected or protected from the environment of the stomach by, for example, coatings, well-known to those skilled in the art. Such a coating may be called for even in the presence of an amide bond between the carrier and the drug.

The compounds of the invention can be prepared in pharmaceutical preparations containing the compounds themselves and a pharmaceutically acceptable carrier. This pharmaceutically acceptable carrier may be solid or liquid. Examples of liquid carriers include water, an aqueous solution of non-toxic salts, such as sterile physiological solutions of saline, or aqueous solutions containing organic solevents, such as ethanol. Also suitable are emulsions, such as oil - in-water emulsions. Solid carriers include both nutritative carriers, such as sucrose or gelatin, and non-nutritative carriers, such as cellulose or talc.

Slow-release capsules and other protective means are suitable for the oral administration of the compounds of the invention due to the protection afforded against hydrolysis in the gastrointestinal tract. Preferred are those capsules which permit the compounds to bypass the stomach. When the present compounds are to be administered peritoneally, they can be administered by subcutaneous, intramuscular or intravenous injections.

Amounts of the compounds of the invention useful for promoting the uptake of the drug by the brain may vary from individual to individual, as well as varying from the particular disorder being treated and the particular effect desired. Such amounts can be determined by experimentation as is well understood by those skilled in the pharmaceutical arts. For suppressing appetite with Dopamine conjugates, amounts in the range of about 100–20000 micro grams per kilogram body weight are preferred.

Generally, compounds are most active when administered intravenously than by the other preferred routes. However, when an amide bond is used to conjugate the drug and carrier, oral administration of the drug appears to work quite well. In any event, when the conjugates of the invention are used to promote the uptake of a drug into the central nervous system, they are administered to humans in amounts sufficient to promote the crossing of the blood brain barrier. When the therapy involves restoring a deficiency of a neuro-transmitter in a human, the conjugate is administered in an amount sufficient to cause the normalization of the deficiency. When the compounds of the present invention are used for treating Parkinsonism or hyperprolactinemia or for suppressing appetite, then they are administered to a human in need of such treatment in an amount sufficient to affect the desired result.

Administration, of course, may be made by any method which allows the active compound to reach the bloodstream and penetrate through the blood brain barrier. Typical methods include oral, rectal, peritoneal and topical administration of the compounds. When the compounds are administered orally, the composition can be in the form of dragees, tablets, syrups or ampules. When the compounds are administered rectally, the composition can be in the form of a suppository. In addition, when the compounds of the invention are to be administered by topical application, they can be in the form of pomade or a gel.

The ability of the bond between the drug and the carrier to be broken once the prodrug is in the CNS will influence the choice of bonds. Likewise, the desired delivery site in the CNS may affect the choice of bonds as the enzymes responsible for breaking various bonds are concentrated in particular locations.

Variations of the particular carrier described in the preferred embodiment also are contemplated. For example, it has been found that a straight chain fatty acid that does not occur naturally in the brain and having 12 carbon atoms and no double bonds coupled to dopamine does not effectively cross the blood brain barrier and is completely inactive as an appetite-suppressant. Likewise, another straight chain fatty acid that does not occur naturally in the brain and having 22 carbon atoms and no double bonds coupled to dopamine does not effectively cross the blood brain barrier and is essentially inactive as an appetite-suppressant. However, a straight chain fatty acid occurring naturally in the brain and having 18 carbon atoms and 3 double bonds coupled to dopamine is partially active. This molecule crosses the blood brain barrier, and it has some effect on locomotor activity although no substantial effect on appetite. Thus, it appears that the length of the fatty acid, the degree of saturation and whether the fatty acid is naturally occurring in the brain affects the ability of the carrier to be combined with a drug to form a prodrug that will cross the blood brain barrier and effectively deliver and liberate the drug at an active site. The carrier molecule preferably is a straight-chained fatty acid of between 16 and 26 carbon atoms in length. More preferably the carrier molecule is between 16 and 22 carbon atoms in length and occurs naturally in the brain. Among the fatty acids occurring naturally in the brain are those with 16 carbon atoms and 0, 1 or 2 double bonds (C16:0; C16:1 and C16:2), those with 18 carbon atoms and 1, 2 or 3 double bonds (C18:1; C18:2; and C18:3), those with 20 carbon atoms and 1, 2 or 4 double bonds (C20:1; C20:2; and C20:4) and those with 22 carbon atoms and 4, 5 or 6 double bonds (C22:4; C22:5 and C22:6). While the position of the double bonds may be between any of the carbon atoms in the fatty acids, the preferred loci are those which occur naturally in the fatty acids of the CNS. Among the naturally-occurring fatty acids, C16:0 and C22:6 are preferred due to their preference for concentrating in the synaptosomal membranes, with C22:6 most preferred. It also has been found that C18:3 acts above average in its ability to deliver a compound across the blood brain barrier.

In addition to the foregoing fatty acids, branched chain fatty acids having between 16 and 26 carbon atoms may be used, such as for example, the foregoing naturally-occurring fatty acids with methyl, ethyl and isopropyl groups at various positions along the carbon chain. Particular examples include analogues of the naturally-occurring polyisoprenoids (dolicols) such as

Having now fully described this invention, it will be appreciated by those of ordinary skill in the art that the same can be practiced with a wide and equivalent range of compositions, modes of administration, therapeutic treatments and the like, without affecting the spirit or scope of the invention or any embodiment thereof.

What is claimed is:
1. A prodrug compound capable of facilitating the passage of drug across the blood-brain barrier comprising:

wherein D is a nueroactive drug selected from the group consisting of dopamine, serotonin, γ-aminobutyric acid, norepinephrine, apomorphine, histamine, epinephrine, glycine, aspartic acid, glutamic acid, taurine, phefluoramine, amphetamine, met-enkephalin, and diethylpropion.

2. A prodrug as claimed in claim 1 wherein said drug is dopamine.

3. A prodrug as claimed in claim 1 wherein said drug is serotonin.

4. A prodrug as claimed in claim 1 wherein said drug is γ-aminobutyric acid.

5. A prodrug as claimed in claim 1 wherein said drug is apomorphine.

6. A prodrug as claimed in claim 1 wherein said drug is norepinephrine.

7. A prodrug compound as claimed in claim 1 wherein the drug is histamine.

8. A prodrug compound as claimed in claim 1 wherein the drug is epinephrine.

9. A prodrug compound as claimed in claim 1 wherein the drug is glycine.

10. A prodrug compound as claimed in claim 1 wherein the drug is aspartic acid.

11. A prodrug as claimed in claim 1 wherein the drug is glutamic acid.

12. A prodrug as claimed in claim 1 wherein the drug is taurine.

13. A prodrug as claimed in claim 1 wherein the drug is phefluoramine.

14. A prodrug as claimed in claim 1 wherein the drug is amphetamine.

15. A prodrug as claimed in claim 1 wherein the drug is met-enkephalin.

16. A prodrug as claimed in claim 1 wherein the drug is diethylpropion.

17. A prodrug as claimed in any one of claims 2-16 in which the bond between the fatty acid carrier and the drug is an amide bond.

18. A prodrug as claimed in any one of claims 2-16 in which the bond between the fatty acid carrier and the drug is an ester bond.

19. A prodrug as claimed in any one of claims 2-16 further comprising a pharmaceutically acceptable carrier.

20. A prodrug compound as claimed in claim 19 wherein the prodrug is formulated into capsule form suitable for oral administration.

21. A prodrug as claimed in claim 19 wherein the prodrug is coated to permit the bond between the fatty acid and the drug to survive the conditions in the stomach.

22. A prodrug as claimed in any one of claims 2-16 wherein at least one of the hydrogens of the fatty acid carrier is replaced with a methyl, ethyl, or isopropyl substituent.

23. A prodrug as claimed in claim 22 having a BPI index of at least two times the BPI index of the drug molecule.

24. A prodrug compound capable of facilitating the passage of a drug across the blood-brain barrier comprising:

wherein D is a neuroactive drug selected from the group consisting of dopamine, serotonin, γ-aminobutyric acid, norepinephrine, apomorphine, histamine, epinephrine, glycine, aspartic acid, glutamic acid, taurine, phefluoramine, amphetamine, met-enkephalin, and diethylpropion.

25. A prodrug as claimed in claim 24 wherein said drug is dopamine.

26. A prodrug as claimed in claim 24 wherein said drug is serotonin.

27. A prodrug as claimed in claim 24 wherein said drug is γ-aminobutyric acid.

28. A prodrug as claimed in claim 24 wherein said drug is apomorphine.

29. A prodrug is claimed in claim 24 wherein said drug is norepinephrine.

30. A prodrug as claimed in claim 24 wherein the drug is histamine.

31. A prodrug as claimed in claim 24 wherein the drug is epinephrine.

32. A prodrug as claimed in claim 24 wherein the drug is glycine.

33. A prodrug as claimed in claim 24 wherein the drug is aspartic acid.

34. A prodrug as claimed in claim 24 wherein the drug is glutamic acid.

35. A prodrug as claimed in claim 24 wherein the drug is taurine.

36. A prodrug as claimed in claim 24 wherein the drug is phefluoramine.

37. A prodrug as claimed in claim 24 wherein the drug is amphetamine.

38. A prodrug as claimed in claim 24 wherein the drug is met-enkephalin.

39. A prodrug as claimed in claim 24 wherein the drug is diethylpropion.

40. A prodrug as claimed in claim 24 having a BPI index of at least two times BPI index of the drug molecule.

41. A prodrug as claimed in any one of claims 25-39 in which the bond between the fatty acid carrier and the drug is an amide bond.

42. A prodrug as claimed in any one of claims 25-39 in which the bond between the fatty acid carrier and the drug is an ester bond.

43. A prodrug as claimed in any one of claim 25-39 further comprising a pharmaceutically acceptable carrier.

44. A prodrug compound as claimed in claim 43 wherein the prodrug is formulated into capsule form suitable for oral administration.

45. A prodrug compound as claimed in claim 44 wherein the capsule is a slow release capsule.

46. A prodrug compound as claimed in claim 43 wherein the prodrug is formulated into tablet form suitable for oral administration.

47. A prodrug as claimed in claim 43 wherein the prodrug is coated to permit the bond between the fatty acid and the drug to survive the conditions in the stomach.

48. A prodrug as claimed in nay one of claims 25-39 wherein at least one of the hydrogens of the fatty acid carrier is replaced with a methyl, ethyl, or isopropyl substituent.

* * * * *